United States Patent
Djennati et al.

(10) Patent No.: US 9,678,064 B2
(45) Date of Patent: Jun. 13, 2017

(54) IMMUNOASSAY APPARATUS INCORPORATING MICROFLUIDIC CHANNEL

(75) Inventors: Nasser Djennati, Cheshire (GB); Andrew Mitchell, Lancashire (GB)

(73) Assignee: BIO AMD HOLDINGS LIMITED, London Greater London (GB)

( * ) Notice: Subject to any disclaimer, the term of this patent is extended or adjusted under 35 U.S.C. 154(b) by 0 days.

(21) Appl. No.: 13/641,216

(22) PCT Filed: Apr. 14, 2011

(86) PCT No.: PCT/GB2011/050749
§ 371 (c)(1),
(2), (4) Date: Nov. 13, 2012

(87) PCT Pub. No.: WO2011/128696
PCT Pub. Date: Oct. 20, 2011

(65) Prior Publication Data
US 2013/0065324 A1    Mar. 14, 2013

(30) Foreign Application Priority Data

Apr. 14, 2010 (GB) .................. 1006203.2

(51) Int. Cl.
*G01N 33/53* (2006.01)
*B01L 3/00* (2006.01)

(52) U.S. Cl.
CPC ........ *G01N 33/53* (2013.01); *B01L 3/502761* (2013.01); *B01L 2200/0668* (2013.01); *B01L 2300/0816* (2013.01); *B01L 2400/043* (2013.01)

(58) Field of Classification Search
None
See application file for complete search history.

(56) References Cited

U.S. PATENT DOCUMENTS

2004/0018611 A1    1/2004  Ward et al.
2007/0238112 A1*  10/2007  Sohn et al. .............. 435/6

FOREIGN PATENT DOCUMENTS

WO    2005/124345    * 12/2005
WO    2008017829 A1    2/2008

OTHER PUBLICATIONS

Smistrup, K. et al., Magnetic Separation in Microfluidic Systems Using Microfabricated Electromagnets—Experiments and Simulations, Journal of Magnetism and Magnetic Materials, 293, pp. 597-604 (May 2005).*

* cited by examiner

*Primary Examiner* — Rebecca Martinez
(74) *Attorney, Agent, or Firm* — Barlow, Josephs & Holmes, Ltd.

(57) ABSTRACT

An assay apparatus having an assay strip. The assay strip has a first area with a plurality of magnetic particles bonded thereto. The assay strip also has a microfluidic (or nanofluidic) channel or chamber, having a sensing area including one or more magnetic particle traps and a magnetic field source provided adjacent to the sensing area. Introduction of a fluid causes the magnetic particles to become attached to or displaced by a substance of interest, travel along the microfluidic channel to the sensing area and become concentrated in the one or more traps thus providing an indication of the presence or absence of a substance of interest in the fluid. There may be a plurality of traps.

15 Claims, 1 Drawing Sheet

IMMUNOASSAY APPARATUS INCORPORATING MICROFLUIDIC CHANNEL

The present invention relates to an immunoassay apparatus and method for determining the presence of substances of interest in fluids, and including although not exclusively the presence of substances of interest in biological fluids. In particular, the invention relates to an immunoassay apparatus containing therein a specifically designed microfluidic channel or other chamber.

In many medical, biological, manufacturing and other systems there is a requirement to determine the presence and/or concentration of various substances in fluids, including, but not limited to molecules such as proteins, hormones or DNA. In the normal course of analysis immunoassay systems are often employed to measure such molecules. Such immunoassays rely on the presence of a tagged antibody or probe (ligand) which adheres to or binds to a molecule of interest. The presence of the tagged probe is detected and the quantity of probe detected thus related to the concentration of the molecule under analysis. Multiple probe systems with a capture probe or antibody and a second tagged probe or antibody to reveal the captured molecule are common. Probes have been used with tags that are radioactive, enzymatic, fluorescent, chemiluminescent and spectrophotometric or colourimetric. End points of tagged probe measurement can therefore be revealed in a variety of systems including spectrophotometric, electrochemical, radioactive, colourimetric, amperometric or potentiometric.

Magnetic beads have been employed in multiple probe systems as a solid phase for the capture probe, providing a highly mobile bead system with high surface area for capture probe attachment [1]. Secondary probes or antibodies can then be added after molecular attachment to the capture probe and in the commonest application a magnetic field is then used to draw together the beads allowing a concentrate to form where the level of the tag can be measured.

Typically, this is achieved by using suitable sensing electronics to determine the concentration of the probe and hence determining the concentration of the molecule of interest. This can be read directly by sensing the increases in the magnetic field density at positions where the probe tags concentrate as described in our previous application no WO2005/124345. Alternatively, other properties of the tags may be utilised to enable the measurement of the probe concentration, for example light sensing electronics may be used if the tag is fluorescent. It is also possible to provide an indirect reading of the probe concentration by introducing another solution to react with the probe tag producing an effect measurable by suitable sensing electronics (such as the production of light by chemiluminescent reactions with the tag). A further alternative would be to measure the probe concentration by analysis of the incident light falling onto a photovoltaic cell placed at an appropriate position.

It is an object of the present invention to provide a method of determining the presence of substances of interest in a fluid whereby the detection is facilitated by the use of a specially designed microfluidic channel to route the fluidic flow towards a sensing area.

According to a first aspect of the present invention there is provided an assay apparatus comprising: an assay strip having a first area with a plurality of magnetic particles bonded thereto; a microfluidic channel or chamber, having a sensing area comprising one or more magnetic particle traps; and a magnetic field source provided adjacent to the sensing area wherein introduction of a fluid causes the magnetic particles to become attached to or displaced by a substance of interest, travel along the microfluidic channel to the sensing area and become concentrated in the one or more traps thus providing an indication of the presence or absence of a substance of interest in the fluid.

In this manner, the assay apparatus of the present invention may provide a clear signal of the presence of substances of interest. The assay apparatus is ideally suited to a threshold assay or, alternatively, a quantitative response and employing this technique enables rapid analysis of a fluid, and effective analysis of very small volumes of fluid.

The particular design of the microfluidic channel may be adapted to facilitate the routing of the fluid containing the particles and substance of interest from a sample application area towards the sensing area. The particular design of the microfluidic channel may be further adapted to facilitate the routing of excess fluid from the sensing area to an exit point. Apparatus according to the invention can be easily and accurately reproduced for better and more consistent reliability.

The one or more traps may be defined by the profile of the channel geometry in the sensing area. Channel geometry in this trap(s) could consist, for example, of a curve (similar to a U shape) or alternatively a convergence of straight edges (as in a V shape), or enable the creation of a particle dwell/suspension region(s) in the flow path of the fluid.

At the trap(s) the magnetic field source provides a local magnetic field which combines with the trap geometry to preferentially retain free moving magnetic particles within the trap. This results in the accumulation of the magnetic particles and thereby provides a quantifiable indication of the presence or absence of a substance of interest. The quantification of the substance of interest would be determined by the sum of the volume of particles in each and all of the magnetic particle trap regions described. In the event that there are provided a plurality of traps, such traps may fill in sequence as the assay progresses, providing a further quantifiable indication of the presence or absence of a substance of interest.

The sensing area is provided with an orientated external magnetic field by means of a suitable magnetic field source. The magnetic field source is preferably mounted on a surface adjacent to the sensing area. The magnetic field source preferably comprises a permanent magnet or electromagnet positioned on the said surface. In some embodiments, a plurality of magnets or electromagnets may be provided in the sensing area. The use of electromagnets may allow greater control of the magnetic field which may be advantageous in certain situations.

In alternative embodiments, the magnetic field source may comprise a plurality of separate permanent magnets or electromagnets provided such that a rough quantisation of the amount of magnetic particles can be obtained by counting the number of permanent magnets or electromagnets adjacent to which magnetic particles have gathered. In such embodiments, each permanent magnet or electromagnet may be associated with a particular particle trap in a series of particle traps thus enabling the collection of magnetic particles in quantised amounts.

The invention may be implemented in a classic 'displacement array' or 'flow displacement array' and the sensing area may be downstream of the surface with the magnetic particles bonded thereto. The magnetic particles bound to the surface may be released into the fluid by becoming attached to the substance of interest or by being displaced by the substance of interest. This may occur though a specific bonding substance such as an antibody. A sample of the fluid is introduced to this surface which contains the substance of interest in an unknown quantity. Competition for the binding site on the magnetic particle from the substance of interest in the sample will release the magnetic particles into the fluid in proportion to the concentration of the substance of interest in the sample. The immobilised magnetic particles can be bound via any suitable bonding substance to substances of interest, multiple layers of different bonding substances can be used to create suitable sites for competition from substances of interest in the sample.

The sensing area may have a volume of less than 10 µL, preferably less than 5 µL. Alternatively, this method may be used in other assays with volumes greater than 10 µL.

In a further alternative embodiment, the magnetic field source may be aided in the trapping of the magnetic particles by the addition of a capture molecule at certain parts of the assay strip. Said capture molecules can be so placed to aid the kinetics of the assay and increase the electronic signal from the cell.

The trapped magnetic particles may be quantified by any suitable means. This might include electronic components such as a Hall effect sensor, a capacitive measurement circuit or a magnetoresistor. Additionally or alternatively, the trapped magnetic particles may be quantified by the detectable change in incident light falling onto one or more photovoltaic cells in the vicinity of the sensing area.

The fluid described may be a liquid or gas, and may be a biological fluid such as a body fluid.

Substances of interest may include naturally occurring substances, substances that are the result of a chemical or biological reaction, such as drug by-products, and substances introduced into a fluid sample. The substance may be a compound, especially a molecule and could be, for example a protein, hormone or DNA section.

By "magnetic" particles is to be understood particles of non-zero magnetic susceptibility. The or each magnetic particle may be ferromagnetic, diamagnetic, paramagnetic or superparamagnetic. A homogeneous or heterogeneous mixture of such particles may be employed. In one embodiment the or each particle is formed from iron oxide. Particles of size in the range 5 nanometers to 100 micrometers may be used or in some embodiments particles of size in the range 5 nanometers to 50 micrometers may be used.

By "microfluidic" channels is to be understood channels having dimensions of up to a few hundred manometers. Such channels could therefore equally be referred to as "nanofluidic" channels.

The or each particle may become attached to a substance of interest by means of a further substance, which shall be referred to as a bonding substance. The or each particle may be coated with the bonding substance. The bonding substance may be a protein, and in some embodiments it is an antibody or probe (ligand).

The or each magnetic particle may be coated with a material to facilitate adherence of a bonding substance to the particle. A suitable coating material is polystyrene.

By appropriate selection of the bonding substance it is possible to arrange for magnetic particles to attach to a variety of substances of interest or to be displaced by a variety of substances of interest. The or each magnetic particle may be arranged so that it can only become attached to or displaced by a single unit of a substance of interest, for example a single molecule. As such each particle may be provided with a single antibody or capture probe.

Advantageously there is no requirement for a secondary antibody capture site to "collect" the magnetic particles together for sensing. Additionally, there is no requirement for complex alignment systems between sensor and the sensing area to give accuracy and consistency. The microfluidics are designed to guide and focus the particles towards the sensing area where the combination of the microfluidic channel particle trap and the applied magnetic field act to concentrate all free magnetic particles in the sensing area. In a particular embodiment of the present invention, the entire fluidic chamber may be less than 500 nm in depth in order to ensure a monolayer of magnetic particles in flow through the entire microfluidic chamber.

According to a second aspect of the present invention there is provided a method of determining the presence of one or more substances of interest in a fluid, the method comprising the steps of: passing the fluid over a surface having a quantity of magnetic particles bound thereto, the magnetic particles free to be released into solution either in response to the presence of a substance of interest in the fluid or in response to the absence of a substance of interest in the fluid; introducing the fluid and any magnetic particles released into the fluid into a microfluidic channel or chamber, having a sensing area comprising one or more particle traps and a magnetic field source provided adjacent to the sensing area, wherein the released magnetic particles thus become concentrated in the one or more traps thus providing an indication of the presence or absence of a substance of interest in the fluid.

The method of the second aspect of the present invention may incorporate any or all of the features described in respect of the assay apparatus of the first aspect of the present invention, as desired or as appropriate.

The quantification of magnetic particles in the sensing area may be determined using two independent properties of a single detector to increase result confidence. For example, a Hall sensor can act as a magnetic sensor and a light sensor in the same circuit configuration. An advantage of this method of quantification is that two sensors effectively 'look' at exactly the same sample area.

Quantification can also be achieved using another form of double detection. This involves combining a subtraction (differential) reading from the sample area where the particles start the test and a final reading from the sensing area to determine the quantity of particles in the traps.

The apparatus may be used with lab-on-chip technology with magnetic sensors for improved accuracy. Lab-on-chip technology describes the fabrication of a series of chemical or bio-chemical interactions on a single piece of substrate material. The substrate incorporates micro- or nano-fluidic regions that can transport samples, mix in reagents, transport into detection areas as well as other functions. This is combined on the same substrate with integrated electronics for excitation, detection, mobilising the sample. Major advantages of this technique are that only small sample volume are required to conduct the tests, repeatability of the tests due to highly accurate and repeatable placement of key elements, one step test procedure (e.g. no requirement to add further reagents after a particular time period such as 5 minutes) and the low cost manufacture of reliable apparatus.

In order that the invention may be more clearly understood embodiments thereof will now be described by way of example with reference to the accompanying drawings of which:

The assay of the present invention is operable to test a sample for the presence of a substance of interest. For the ease of explanation, the following description will detail an example wherein the present invention is applied to the determination of the presence of HCG 16 (Human chorionic gonadotropin) in a urine sample. A level of HCG above a particular threshold may provide an indication of pregnancy in the sample donor. It is of course obvious to the skilled man that the assay of the present invention could be suitably adapted to test for the presence of other substances of interest of or other types of sample.

Figure 1:
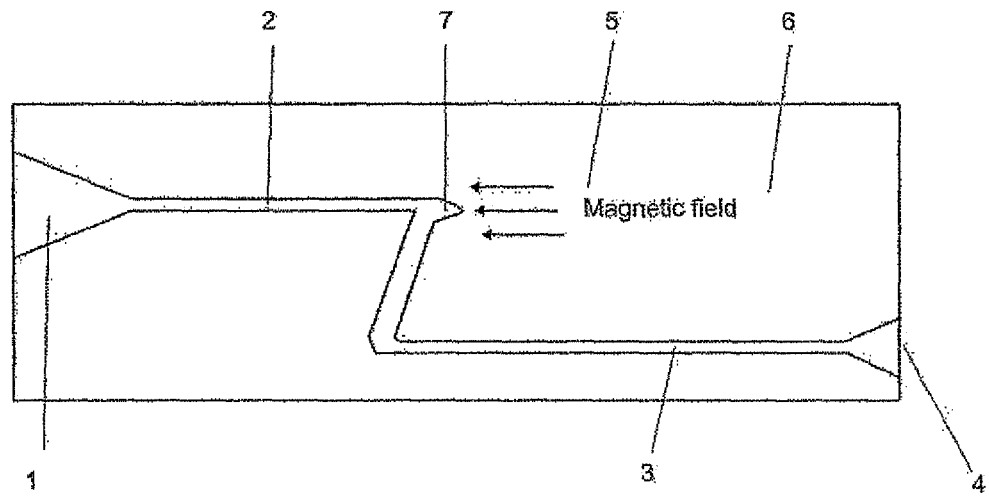
FIG. 1 is a schematic view of a first embodiment of assay apparatus for performing the present invention.
Figure 2:
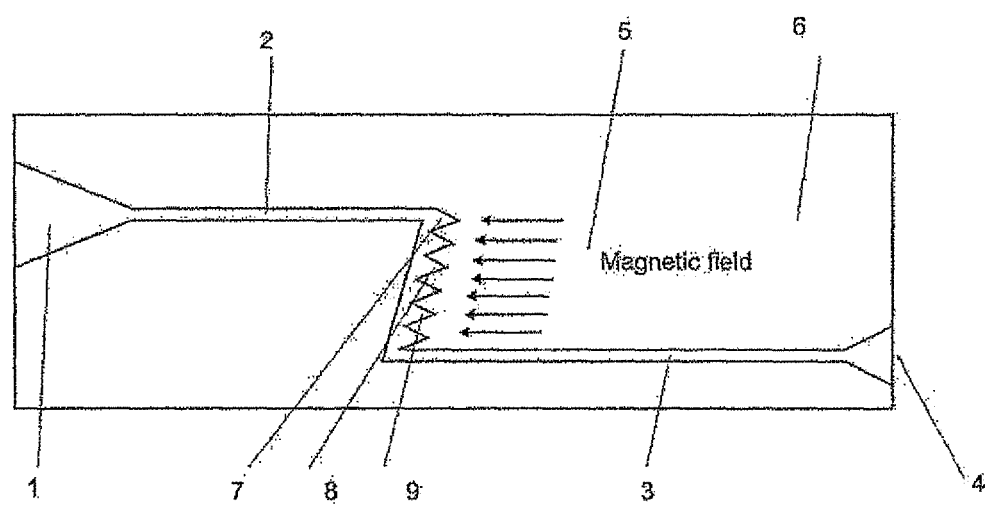
FIG. 2 is a schematic view of a first embodiment of assay apparatus for performing the present invention.

Referring now to FIGS. 1 and 2 which show two alternative embodiments, the urine sample is added to an application area (1) on the assay strip (6). The sample flows along a microfluidic channel on the assay strip (6). The flow along the microfluidic channel is first over an area (2) containing pre-deposited HCG or HCG analogue. The pre-deposited HCG or HCG analogue (2) is labelled with magnetic particles that contain a specific probe for the HCG molecule. During the flow, by kinetics or preferential binding, the magnetic particles become bound to free HCG in the sample to produce magnetic HCG complexes which are released into the solution.

The flow along the microfluidic channel next passes a sensing area comprising either a single magnetic particle trap (7) as shown in FIG. 1 or multiple magnetic particle traps (7,8,9, . . . ) as shown in FIG. 2. Each trap (7,8,9, . . . ) comprises a deviation in the profile of the microfluidic channel geometry in the sensing area. In the particular examples shown each trap (7,8,9, . . . ) comprises a convergence of straight edges (as in a V shape) which provides a particle dwell/suspension region in the flow path of the fluid.

Adjacent to the sensing area (7,8,9) is provided a magnetic field source (5). The magnetic field source (5) is typically a permanent magnet or electromagnet placed beneath the assay strip (6). The magnetic field source (5) provides a magnetic field that acts to draw the magnetic complexes through the solution towards the magnet (5). At the traps (7,8,9, . . . ) the local magnetic field combines with the trap geometry to preferentially retain free moving magnetic particles within the traps (7,8,9). This results in the accumulation of the magnetic particles and thereby provides a quantifiable indication of the presence or absence of a substance of interest.

After passing the traps (7,8,9, . . . ), which can be provided within the strip to minimise the chances of any particle escaping the detection area, the excess sample fluid is then routed by capillary action along the microfluidic channel (3) to the exit point (4).

Figure 3:
FIG. 3 is cross-sectional view of apparatus of FIGS. 1 and 2.

As is illustrated in FIG. 3, the assay strip (6) may be provided with a lid (10) and base (11). Either or both of the lid (10) and base (11) may be formed from plastic material of a hydrophilic nature.

In an alternative implementation, the magnetic particles and HCG probe could have been separately introduced to the urine sample before the sample flowed over the bound HCG or HCG analogue (2). In this mode the free magnetic particles, which have not bound to the HCG in the sample, will then bind to the surface deposited HCG or surface deposited HCG analogue and be removed from flow in the strip. In such circumstances, the amount of complexes drawn to the magnet are in proportion to the amount of HCG in the donor's sample.

It is of course to be understood that the invention is not to be restricted to the details of the above embodiments which have been described by way of example only.

REFERENCES

1. "Application of magnetic techniques in the field of drug discovery and biomedicine" Z M Saiye, S D Telang and C N Ramchand, *BioMagnetic Research and Technology* Volume 1

The invention claimed is:

1. An assay apparatus comprising:
   an assay strip having a nanofluidic channel formed therein,
   said nanofluidic channel having a first tagging area with a plurality of magnetic particles releasably bonded thereto, said magnetic particles comprising a specific bonding substance that is chosen to bond to a substance of interest in a fluid, said magnetic particles having a predetermined size,
   said nanofluidic channel further having a sensing area comprising a plurality of magnetic particle traps configured and arranged to retain said magnetic particles therein,
   said sensing area being downstream of said first tagging area,
   said nanofluidic channel having a predetermined depth and configuration corresponding to said predetermined size of said magnetic particles whereby only a monolayer of magnetic particles in said fluid may flow through the entire nanofluidic channel; and
   an external magnetic field source adjacent to and outside of the sensing area,
   said fluid traveling along the nanofluidic channel in a monolayer from the tagging area to the sensing area where said magnetic particles become concentrated in the plurality of magnetic particle traps,
   said plurality of magnetic particle traps being spaced apart along a primary flow direction of said fluid through said sensing area, so that said plurality of magnetic particle traps define a series of ridges and troughs when viewed in a direction perpendicular to said primary flow direction of said fluid through said sensing area, and so that said plurality of magnetic particle traps are arranged in said nanofluidic channel to fill in sequence as said fluid progresses through said nanofluidic channel,
   said magnetic particles being sensed while trapped in said magnetic particle traps to provide an indication of the presence or absence of said substance of interest.

2. An assay apparatus as claimed in claim 1, wherein said plurality of magnetic particle traps are defined by the profile of the channel geometry in the sensing area.

3. An assay apparatus as claimed in claim 1, wherein the channel geometry is chosen to create a particle dwell/suspension region(s) in the flow path of the fluid.

4. An assay apparatus as claimed in claim 1, wherein the magnetic field source provides a local magnetic field at said plurality of magnetic particle traps which combines with the trap geometry to preferentially retain free moving magnetic particles within said plurality of magnetic particle traps.

5. An assay apparatus as claimed in claim 1, wherein the sensing area has a volume of less than 10 μL.

6. An assay apparatus as claimed in claim 1, further comprising a capture molecule on said assay strip to aid the magnetic field source in the trapping of the magnetic particles.

7. An assay apparatus as claimed in claim 1, further comprising at least one electronic component selected from the group consisting of: a Hall Effect sensor, a capacitive measurement circuit and a magnetoresistor to measure the quantity of magnetic particles in sensing area.

8. An assay apparatus as claimed in claim 1, further comprising one or more photovoltaic cells.

9. An assay apparatus as claimed in claim 1, wherein each of said plurality of magnetic particles is a magnetic particle selected from the group consisting of: ferromagnetic, diamagnetic, paramagnetic and superparamagnetic.

10. An assay apparatus as claimed in claim 1, wherein each of said plurality of magnetic particles is coated with the bonding substance.

11. An assay apparatus as claimed in claim 1, wherein the bonding substance is an antibody or probe (ligand).

12. An assay apparatus as claimed in claim 1 wherein each of said plurality of magnetic particles is coated with a material to facilitate adherence of a bonding substance to the particle.

13. An assay apparatus as claimed in claim 12, wherein the coating material is polystyrene.

14. An assay apparatus as claimed in claim 1 wherein the dimensions of the nanofluidic channel are less than 500 nm.

15. An assay apparatus as claimed in claim 1 wherein said nanofluidic channel has a depth of less than 500 nm.

* * * * *